(12) United States Patent
Ulmsten (10) Patent No.: US 7,658,743 B2
(45) Date of Patent: *Feb. 9, 2010

(54) SURGICAL INSTRUMENT AND METHOD FOR TREATING FEMALE URINARY INCONTINENCE

(75) Inventor: Ulf Ulmsten, Dandervd (SE)

(73) Assignee: Ethicon, Inc., Somerville, NJ (US)

( * ) Notice: Subject to any disclaimer, the term of this patent is extended or adjusted under 35 U.S.C. 154(b) by 539 days.

This patent is subject to a terminal disclaimer.

(21) Appl. No.: 10/179,364

(22) Filed: Jun. 25, 2002

(65) Prior Publication Data

US 2002/0165566 A1 Nov. 7, 2002

Related U.S. Application Data

(63) Continuation of application No. 09/051,311, filed as application No. PCT/SE96/01269 on Oct. 8, 1996, now Pat. No. 6,491,703.

(51) Int. Cl.
*A61B 17/08* (2006.01)
(52) U.S. Cl. ......................... 606/151; 600/30
(58) Field of Classification Search .................. 128/898; 600/29, 37
See application file for complete search history.

(56) References Cited

U.S. PATENT DOCUMENTS

| | | | |
|---|---|---|---|
| 2,993,589 A | 7/1961 | Zoller et al. | |
| 3,038,475 A | 6/1962 | Orcutt | |
| 3,182,662 A | 5/1965 | Shirodkar | |
| 3,212,502 A | 10/1965 | Myers | |
| 3,311,110 A | 3/1967 | Singerman et al. | |
| 3,472,232 A | 10/1969 | Earl | |
| 3,608,095 A | 9/1971 | Barry | |
| 3,763,860 A | 10/1973 | Clarke | |
| 3,858,783 A | 1/1975 | Kapitanov et al. | |
| 3,924,633 A | 12/1975 | Cook et al. | |
| 4,037,603 A | 7/1977 | Wendorff | |
| 4,128,100 A | 12/1978 | Wendorff | |
| 4,235,238 A | 11/1980 | Ogiu et al. | |

(Continued)

FOREIGN PATENT DOCUMENTS

AU 278089 6/1965

(Continued)

OTHER PUBLICATIONS

Petros, P.E. Papa "Vault Prolapse II: Restoration of Dynamic Vaginal Supports by Infracoccygeal Sacropexy, an Axial Day-Case Vaginal Procedure", International Urogynecol Journal, Springer-Verlag London Ltd., 2001, vol. 12, pp. 296-303.

(Continued)

*Primary Examiner*—Anhtuan T Nguyen
*Assistant Examiner*—Tuan V Nguyen (57) ABSTRACT

The method of the present invention relates to treating female urinary incontinence and involves passing opposite ends of a tape into a female patient's body and then positioning at least a portion of the tape between the vaginal wall and the urethra, whereby the tape forms a supportive loop beneath the urethra. The ends of the tape are extended through the patient's abdominal wall and outside of the patient's body and then the position and tension of the supportive loop are adjusted to achieve a clinically acceptable degree of urinary continence.

14 Claims, 12 Drawing Sheets

U.S. PATENT DOCUMENTS

| | | | |
|---|---|---|---|
| 4,392,495 A | 7/1983 | Bayers |
| 4,441,497 A | 4/1984 | Paudler |
| 4,455,690 A | 6/1984 | Homsy |
| 4,509,516 A | 4/1985 | Richmond |
| 4,549,545 A | 10/1985 | Levy |
| 4,668,233 A | 5/1987 | Seedhom et al. |
| 4,775,380 A | 10/1988 | Seedhom et al. |
| 4,946,467 A | 8/1990 | Ohi et al. |
| 5,013,292 A | 5/1991 | Lemay |
| 5,019,032 A | 5/1991 | Robertson |
| 5,032,508 A | 7/1991 | Naughton et al. |
| 5,080,567 A | 1/1992 | Chen et al. |
| 5,112,344 A | 5/1992 | Petros |
| 5,122,155 A | 6/1992 | Eberbach |
| 5,149,329 A | 9/1992 | Richardson |
| 5,180,385 A | 1/1993 | Sontag |
| 5,250,033 A | 10/1993 | Evans et al. |
| 5,281,237 A | 1/1994 | Gimpelson |
| 5,364,408 A | 11/1994 | Gordon |
| 5,368,595 A | 11/1994 | Lewis |
| 5,368,756 A | 11/1994 | Vogel et al. |
| 5,382,257 A | 1/1995 | Lewis et al. |
| 5,383,904 A | 1/1995 | Totakura et al. |
| 5,403,328 A | 4/1995 | Shallman |
| 5,450,860 A | 9/1995 | O'Connor |
| 5,458,609 A | 10/1995 | Gordon et al. |
| 5,507,796 A | 4/1996 | Hasson |
| 5,540,704 A | 7/1996 | Gordon et al. |
| 5,575,800 A | 11/1996 | Gordon |
| 5,578,044 A | 11/1996 | Gordon et al. |
| 5,582,188 A | 12/1996 | Benderev |
| 5,611,515 A | 3/1997 | Benderev et al. |
| 5,628,756 A | 5/1997 | Barker, Jr. et al. |
| 5,645,568 A | 7/1997 | Chervitz et al. |
| 5,662,664 A | 9/1997 | Gordon et al. |
| 5,671,695 A | 9/1997 | Schroeder |
| 5,700,272 A | 12/1997 | Gordon et al. |
| 5,713,910 A | 2/1998 | Gordon et al. |
| 5,741,277 A | 4/1998 | Gordon et al. |
| 5,741,279 A | 4/1998 | Gordon et al. |
| 5,741,299 A | 4/1998 | Rudt |
| 5,816,258 A | 10/1998 | Jervis |
| 5,836,315 A | 11/1998 | Benderev et al. |
| 5,840,011 A | 11/1998 | Landgrebe et al. |
| 5,855,549 A | 1/1999 | Newman |
| 5,860,425 A | 1/1999 | Benderev et al. |
| 5,871,536 A | 2/1999 | Lazarus |
| 5,899,909 A * | 5/1999 | Claren et al. ............ 606/119 |
| 5,899,999 A | 5/1999 | DeBonet |
| 5,935,122 A | 8/1999 | Fourkas et al. |
| 5,945,122 A | 8/1999 | Abra et al. |
| 5,954,057 A | 9/1999 | Li |
| 5,997,554 A | 12/1999 | Thompson |
| 6,048,351 A | 4/2000 | Gordon et al. |
| 6,110,101 A | 8/2000 | Tihon et al. |
| 6,117,067 A | 9/2000 | Gil-Vernet |
| 6,221,005 B1 | 4/2001 | Bruckner et al. |
| 6,273,852 B1 | 8/2001 | Lehe et al. |
| 6,306,079 B1 | 10/2001 | Trabucco |
| 6,334,446 B1 | 1/2002 | Beyar |
| 6,346,111 B1 | 2/2002 | Gordon et al. |
| 6,382,214 B1 | 5/2002 | Raz et al. |
| 6,475,139 B1 | 11/2002 | Miller |
| 6,491,703 B1 | 12/2002 | Ulmsten |
| 6,605,097 B1 | 8/2003 | Lehe et al. |
| 7,033,370 B2 | 4/2006 | Gordon et al. |
| 7,060,077 B2 | 6/2006 | Gordon et al. |
| 7,347,813 B2 * | 3/2008 | Claren et al. ............ 600/30 |
| 2001/0018549 A1 | 8/2001 | Scetbon |
| 2001/0023352 A1 | 9/2001 | Gordon et al. |
| 2001/0049467 A1 | 12/2001 | Lehe et al. |
| 2002/0028980 A1 | 3/2002 | Thierfelder et al. |
| 2002/0058959 A1 | 5/2002 | Gellman |
| 2002/0077526 A1 | 6/2002 | Kammerer et al. |
| 2002/0091373 A1 | 7/2002 | Berger |
| 2002/0188169 A1 | 12/2002 | Kammerer et al. |
| 2003/0023138 A1 | 1/2003 | Luscombe |
| 2003/0149440 A1 | 8/2003 | Kammerer et al. |
| 2003/0176762 A1 | 9/2003 | Kammerer |
| 2004/0059350 A1 | 3/2004 | Gordon et al. |

FOREIGN PATENT DOCUMENTS

| | | |
|---|---|---|
| AU | 441561 | 1/1972 |
| DE | 3223153 C | 8/1983 |
| DE | 4220283 A1 | 12/1993 |
| DE | 4334419 | 4/1995 |
| DE | 10103179 A1 | 7/2001 |
| EP | 0 153 831 A2 | 9/1985 |
| EP | 0 223 370 A2 | 5/1987 |
| EP | 0 597 446 A1 | 5/1994 |
| EP | 0598 976 A2 | 6/1994 |
| EP | 0668056 A1 | 8/1995 |
| EP | 0774240 A1 | 5/1997 |
| EP | 0 852 930 A2 | 7/1998 |
| EP | 0941712 A1 | 9/1999 |
| EP | 0598976 | 7/2000 |
| EP | 1025811 A2 | 8/2000 |
| EP | 1 151 722 A2 | 11/2001 |
| SE | 503271 | 4/1996 |
| WO | 9003766 | 4/1990 |
| WO | WO 94/05213 A1 | 3/1994 |
| WO | WO95/13033 | 5/1995 |
| WO | 9606567 | 3/1996 |
| WO | WO97/13465 | 4/1997 |
| WO | 9831301 A1 | 7/1998 |
| WO | WO 00/74613 A1 | 12/2000 |
| WO | WO 01/06951 A1 | 2/2001 |
| WO | 02/28312 A | 4/2002 |
| WO | WO 0238079 A2 | 5/2002 |
| WO | 2004/012626 | 3/2004 |

OTHER PUBLICATIONS

Petros, P.E. Papa "Vault Prolapse I: Dynamic Supports of the Vagina", International Urogynecol Journal, Springer-Verlag London Ltd.., 2001, vol. 12, pp. 292-295.

"TVT Tension-free Vaginal Tape, Minimally Invasive, Highly effective Treatment for Female Stress Urinary Incontinence", Gyncare, Ethicon, Inc., 1999, pp. 1-6.

"AMS Sparc Sling System", American Medical Systems, Inc., Minnetonka, MN, 2001, pp. 1-6.

Leanza, V. et al., New Technique For Correcting Both Incontinence And Cystocele: T.I.C.T. (Tension-free Incontinence Cystocele Treatment) Urogynaecologia International Journal, 2001, No. 3515, pp. 133-140.

Collinet, P. et al., "The Vaginal Patch For Vaginal Cure Of Cystocele", J. Cynecol. Obstet. Biol. Reprod. vol. 29, No. 2, (2000), pp. 197-201.

Cosson, M. et al., "Cystocele Repair By Vaginal Patch", Progres en Urologie, 2001, 11, pp. 340-346.

Giberti, C. "Transvaginal Sacrospinous Colpoplexy By Palpation—A New Minimally Invasive Procedure Using An Anchoring System", Urology, 57(4), 666-668 (2001), Elsevier Science Inc., Ospedale.

Kersey, "The Gauze Hammock Sling Operation in Treatment of Stress Incontinence," British Journal of Obstetrics and Gynaecology, Oct. 1983, vol. 90, pp. 945-949.

Petros et al., "An Integral Theory of Female Urinary Incontinence," Ada Obstet. Gynecol. Scand., 1990, vol. 69, Suppl. 153, pp. 43-51, Almqvist & Wiksell Intl., Sweden.

Petros et al., "An integral Theory and its Method for the Diagnosis and Management of Female Urinary Incontinence," Scand. J. Urol. Nephrol, vol. 69, Suppl.153,1993, pp. 77-79.

Petros, "Ambulatory Surgery for Urinary Incontinence and Vaginal Prolapse," The Medical Journal of Australia, vol. 161, Jul., 1994, pp. 171 and 172.

Ulmsten at al., "Intravaginal Slingplasty," Zentralbi Gynakol 116, 1994, pp. 398-404.

Ulmsten et al., "An Ambulatory Surgical Procedure Under Local Anesthesia for Treatment of Female Urinary Incontinence," Int. Urogynecol J., 1996, vol. 7, pp. 81-86.

Brenner, "Mesh Materials in Hernia Repair," a printout (one page) from the following website, http://www.herniasolutions.com/professional/clin.html.

Medcompare, "MERSILENE Polyester Fiber Mesh," a printout (one page) from the following website, http://www.medcompare.com/itemdetails.asp?itemid=35861.

European Patent Office Examination Report issued in European Patent Application No. 01 990 938, Jul. 27, 2007.

* cited by examiner

FIG. 14

SURGICAL INSTRUMENT AND METHOD FOR TREATING FEMALE URINARY INCONTINENCE

CROSS-REFERENCE TO RELATED APPLICATION

This application is a continuation application of U.S. application Ser. No. 09/051,311, filed Jul. 27, 1998, now U.S. Pat. No. 6,491,703, which was the National Stage of International Application No. PCT/SE96/01269, filed Oct. 8, 1996 and published in the English language.

FIELD OF THE INVENTION

The invention relates to a surgical instrument and a method using same for treating female urinary incontinence.

BACKGROUND OF THE INVENTION

U.S. Pat. No. 5,112,344 discloses a surgical incontinence device and method, wherein the disclosed device includes a shank having a handle at one end thereof, and a curved needle-like element which is constructed to be connected with the shank to form a curved portion.

WO-A-9606567, the content of which is hereby incorporated by reference herein, discloses a surgical incontinence device that allows for alleviating female urinary incontinence while restoring continence by attaching two curved needles to a tape that is intended to be permanently implanted into the tissue between the vaginal wall and the abdominal wall of a patient, thus strengthening the tissue required to restore the urinary continence. The method disclosed in WO-A-9606567 involves the steps of passing the tape into the tissue between the vaginal wall and the abdominal wall and leaving the tape permanently in the body, thereby providing reinforcement of the tissue that is required to restore urinary continence, either by the tape itself acting as an artificial ligament or by the development of fibrous tissue.

BRIEF SUMMARY OF THE INVENTION

The method of the present invention relates to treating female urinary incontinence and involves passing the first and second ends of a tape into a female patient's body and then positioning at least a portion of the tape between the vaginal wall and the urethra. After such positioning, the tape forms a supportive loop beneath the urethra. The ends of the tape are then extended over the patient's pubic bone and through her abdominal wall such that the ends of the tape extend outside of the patient's body. The position and tension of the supportive loop are adjusted to achieve a clinically acceptable degree of urinary continence. The ends of the tape may be passed into the patient's body via the vagina. The tape may be at least partially enclosed by a removable sheath, which is removed after the tape is positioned and adjusted.

BRIEF DESCRIPTION OF THE DRAWINGS

The invention will be explained in more detail with reference to the accompanying drawings which disclose the surgical instrument according to the invention and wherein.

DETAILED DESCRIPTION OF THE INVENTION

In the following description, the same reference numerals have been used to describe the various features of the instrument of the present invention as were used in WO-A-9606567. To facilitate the following discussion, however, the order of the figures has been changed and the reference numerals used to describe the female urinary system have been altered.

With reference to FIGS. 1-6, the surgical instrument of the present invention comprises a cylindrical tubular shank 10 having at one end thereof a handle 11. At the other end of the shank there is a socket 14. A cylindrical shaft 15 (see FIGS. 2 and 5) is rotatably mounted in the shank and can be rotated manually by means of a knob 16 mounted to one end of the shaft. The other end of the shaft 15 forms a cylindrical portion 17 (see FIG. 5) of smaller outside diameter than the shaft, which joins a portion 18 having external threads, a smooth end portion 19 of further reduced diameter joining the threaded portion 18, end portion 19 forming a guide pin at said other end of the shaft. Portions 18 and 19 are received in the portion of socket 14 projecting from the shank. The surgical instrument as described so far is in agreement with the instrument disclosed in WO-A-9606567 except that the end portion 14' of socket 14 is flattened from opposite sides (see FIGS. 1 and 2), so that the cross section of said end portion is non-circular.

The surgical instrument also includes an exchangeable and disposable needle 21 which at one end thereof is attached to the shank at one end of the needle and extends over substantially a quarter of a circle to the other, free end thereof in order to follow substantially the profile of the pubis between the vagina and the abdominal wall. The needle has uniform circular cross section and has a smooth, preferably polished outside surface. At the free end thereof the needle forms a point 22 by being terminated by a conical portion.

For attachment of needle 21 to shank 10 the needle forms at said one end thereof a straight portion 30 which is cylindrical but has milled flat faces 31 (see FIG. 3) over that part of said portion 30, extending from the adjacent end of the needle, which shall be received by socket portion 14'. The needle should be oriented in a predetermined rotational position in relation to the shank, and more particularly it should project at right angles to the plane of handle 11. This rotational position is secured by the non-circular shape of socket portion 14' and the end portion of the needle having the flat faces 31, which fits into socket portion 14'. The end portion of the needle having the flat faces 31 joins the body of the needle over the conical portion 32, which tapers towards a shoulder 33 (see FIG. 3).

An axial blind hole extends from the end surface of the needle said hole having a threaded portion 23 and inwardly thereof a narrower, cylindrical portion 24. Guide pin 19 is dimensioned to be guidingly received by said latter portion when the threaded portion 18 for attaching needle 21 to the rest of the surgical instrument is screwed into threaded portion 23 of the blind hole by rotating shaft 15 by manual rotation of knob 16, the end surfaces of the shank and the needle being pressed against each other. Also this attachment is in agreement with that described in WO-A-9606567.

Figure 1:
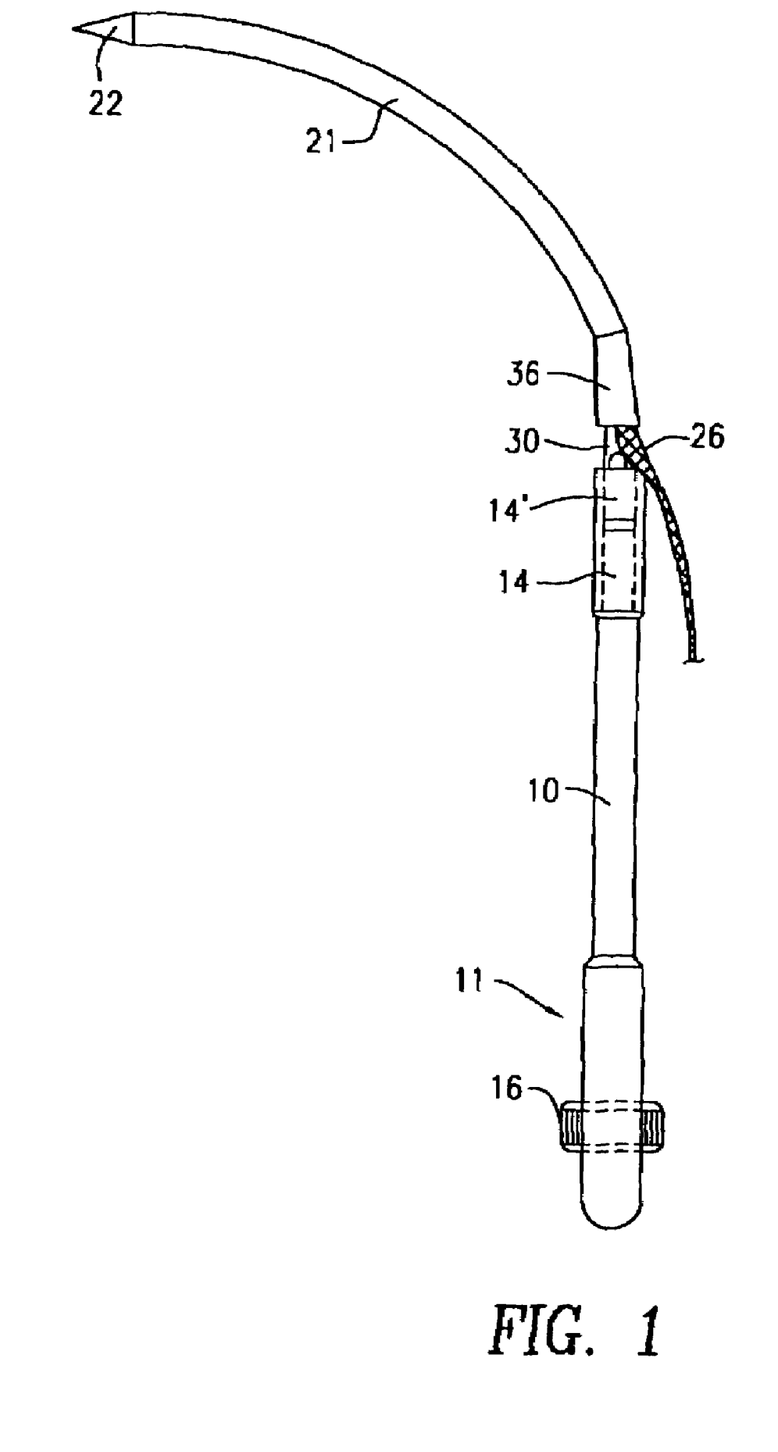
FIG. 1 is a side view of the surgical instrument according to the invention.
Figure 2:
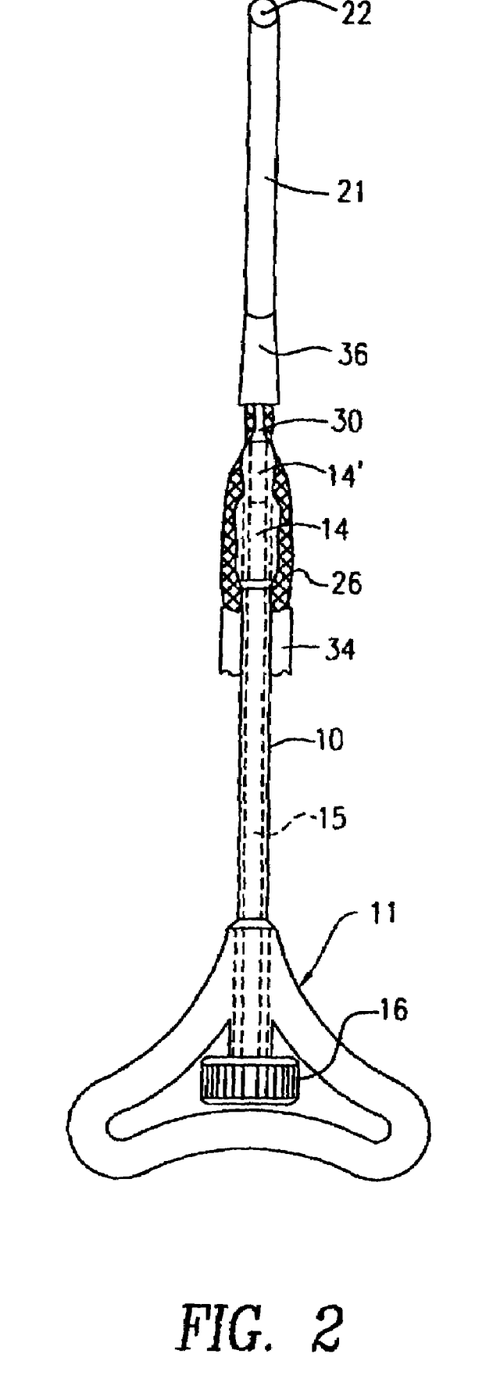
FIG. 2 is a plan view of the surgical instrument.
Figure 3:
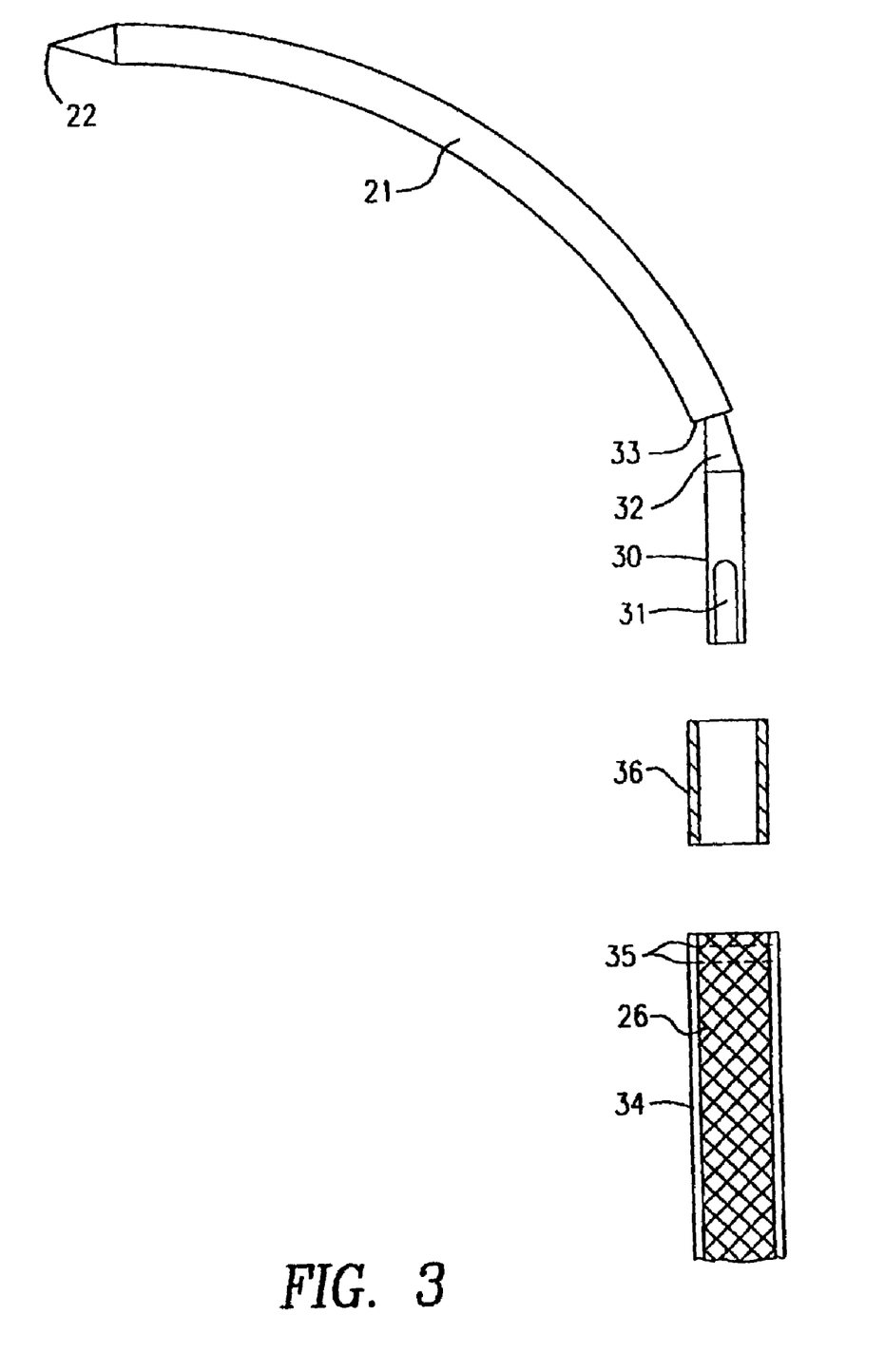
FIG. 3 is an exploded side view of one of the needles and tape and shrinkage hose to be connected with said needle.
Figure 4:
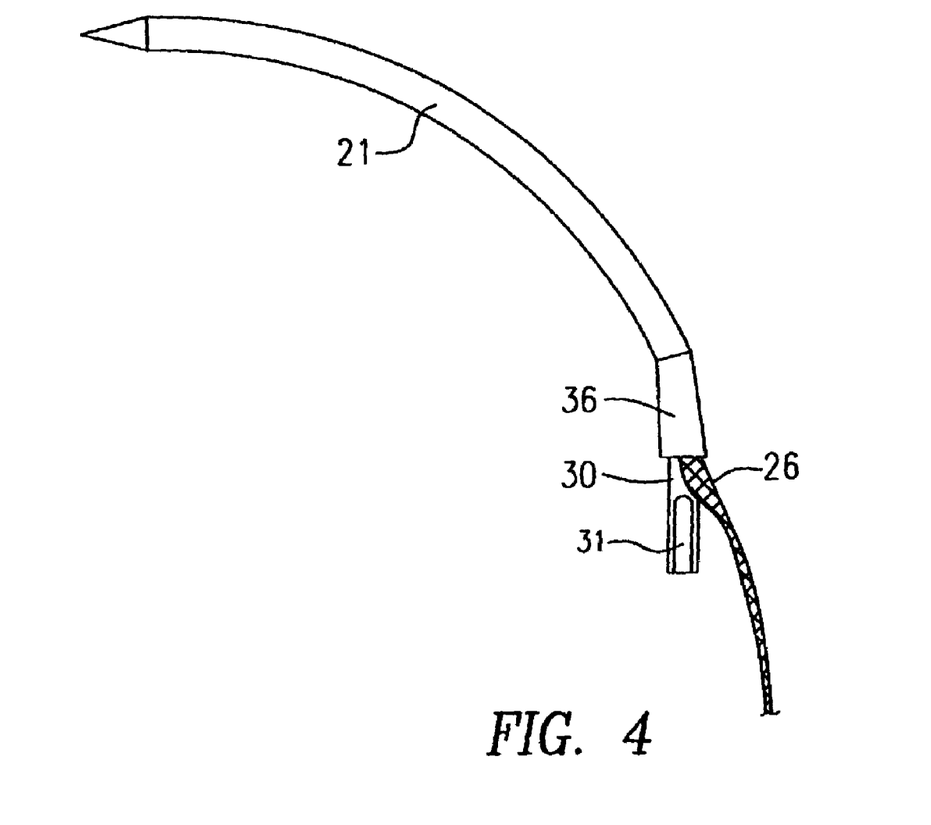
FIG. 4 is a side view of the needle in FIG. 3 with the tape connected therewith.
Figure 5:
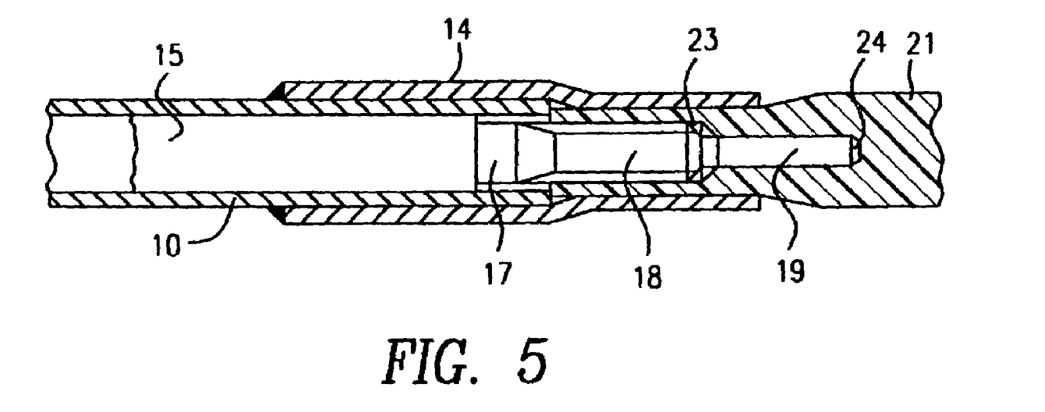
FIG. 5 is an enlarged fragmentary axial cross sectional view of a coupling of the instrument for connecting an exchangeable needle thereof.

When the method as described in WO-A-9606567 is practiced, two needles 21A and 21B (see FIG. 6) are each connected to each end of a tape 26. According to the present invention, the tape 26 of the preferred embodiment comprises a mesh or netting forming openings of the order of 1 mm. A suitable material for the tape 26 is PROLENE®, a knitted polypropylene mesh having a thickness of 0.7 mm manufactured by Ethicon, Inc., Sommerville, N.J., USA. This material is approved by FDA in USA for implantation into the human body. The netting (tape) 26 preferably has a width of approximately 10 mm and is enclosed in a thin polyethylene sheath 34 which, in flattened condition, has substantially the same width as the tape 26 although a difference in width is shown in FIG. 2 in order to make the provision of the sheath 34 more clear. The length of the netting 26 should be approximately 400 mm. The netting 26 and the sheath 34 are interconnected by means of two rows 35 of stitching. The end portion of the sheath 34 is attached to the conical portion 32 (see FIG. 3) of the needle 21 by means of a suitable strong glue, and the interconnection of the needle 21 and sheath 34 is covered by a shrink hose 36 (see FIGS. 3 and 4) made of rubber, which extends from the shoulder 33 over the conical portion 32 and partly over the cylindrical end portion 30 of the needle 21. The shrink hose 36 is substantially flush with the surface of the needle 21 at the shoulder 33. By this arrangement the netting 26 is securely attached to the needle 21.

The purpose of sheath 34 is, above all, to facilitate the insertion of the netting 26 in the manner described in WO-A-9606567, i.e., when the netting 26 is pulled at the ends thereof from the vaginal wall to the abdominal skin and to avoid that rough edges of the netting irritate or damage the body tissues.

When the tape has been positioned in the correct position as a sling around the urethra (as described hereinafter in connection with the method of the present invention shown in FIGS. 7-14) the polyethylene sheath 34 shall be removed, and in order to facilitate the removal the sheath 34 should be perforated at the longitudinal center thereof as indicated by a dot-and-dash line 37 in FIG. 6, so that the two halves of the sheath 34 can be withdrawn from the body by pulling at the respective outer ends thereof, the halves being separated at the perforation under the influence of the pulling force.

The purpose of the polyethylene sheath 34 is also to protect the netting 26 during attachment to the needles 21A, 21B and during handling before and during insertion into the body.

Figure 6:
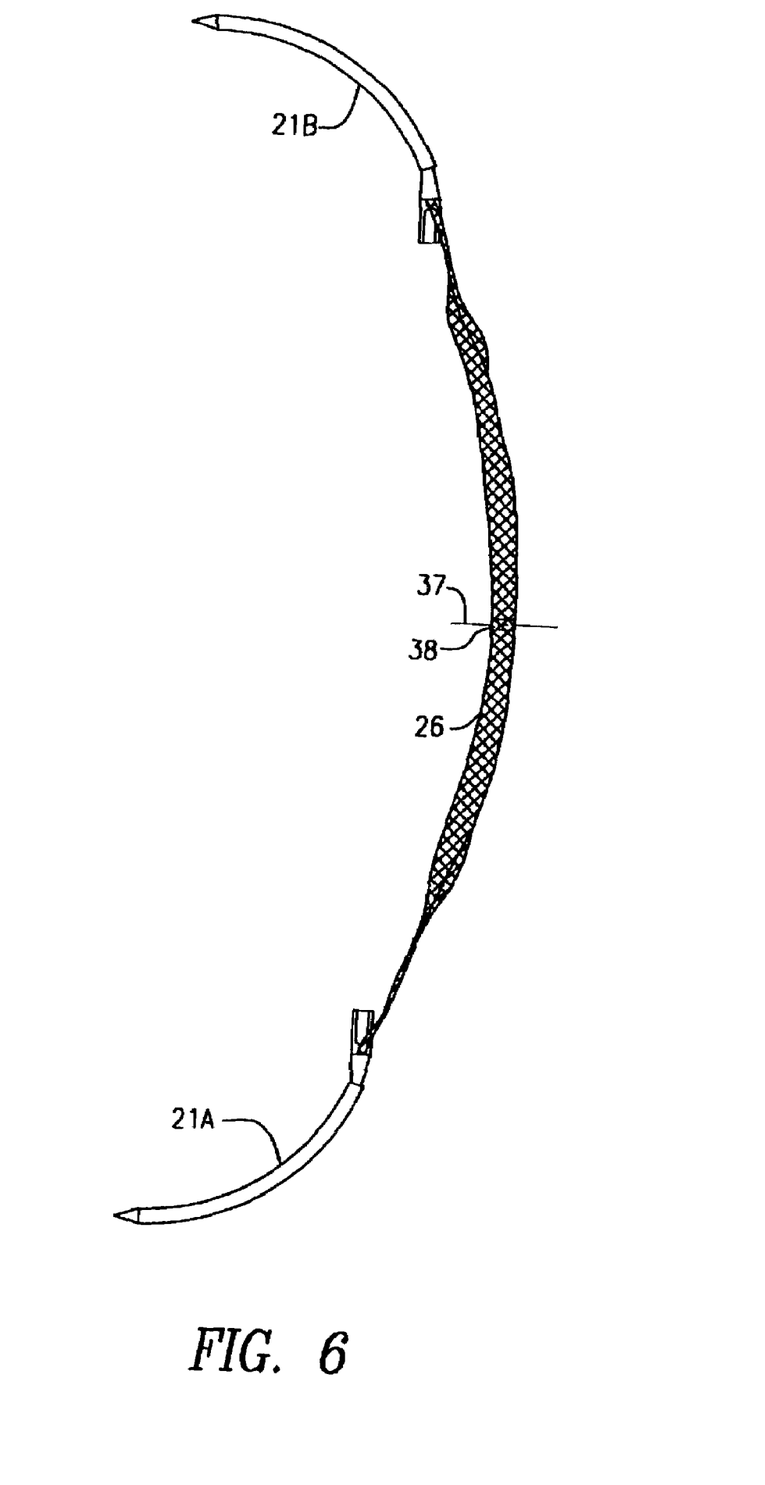
FIG. 6 is a side view of the two needles and a tape interconnecting said needles.

The longitudinal center of the tape 26 and sheath 34 should be indicated by a visible colour mark 38, (see FIG. 6, so that the surgeon readily can see when the netting 26 is symmetrically located with reference to urethra during the surgery.

The method of the present invention will now be described in detail with reference to FIGS. 7-14. In FIGS. 7-14, the relevant parts of the female lower abdomen are disclosed diagrammatically, the vagina being designated 40, the vaginal wall 42, the urinary bladder 44, the urethra 46, the pubic bone 48, and the abdominal wall 50.

Figure 7:
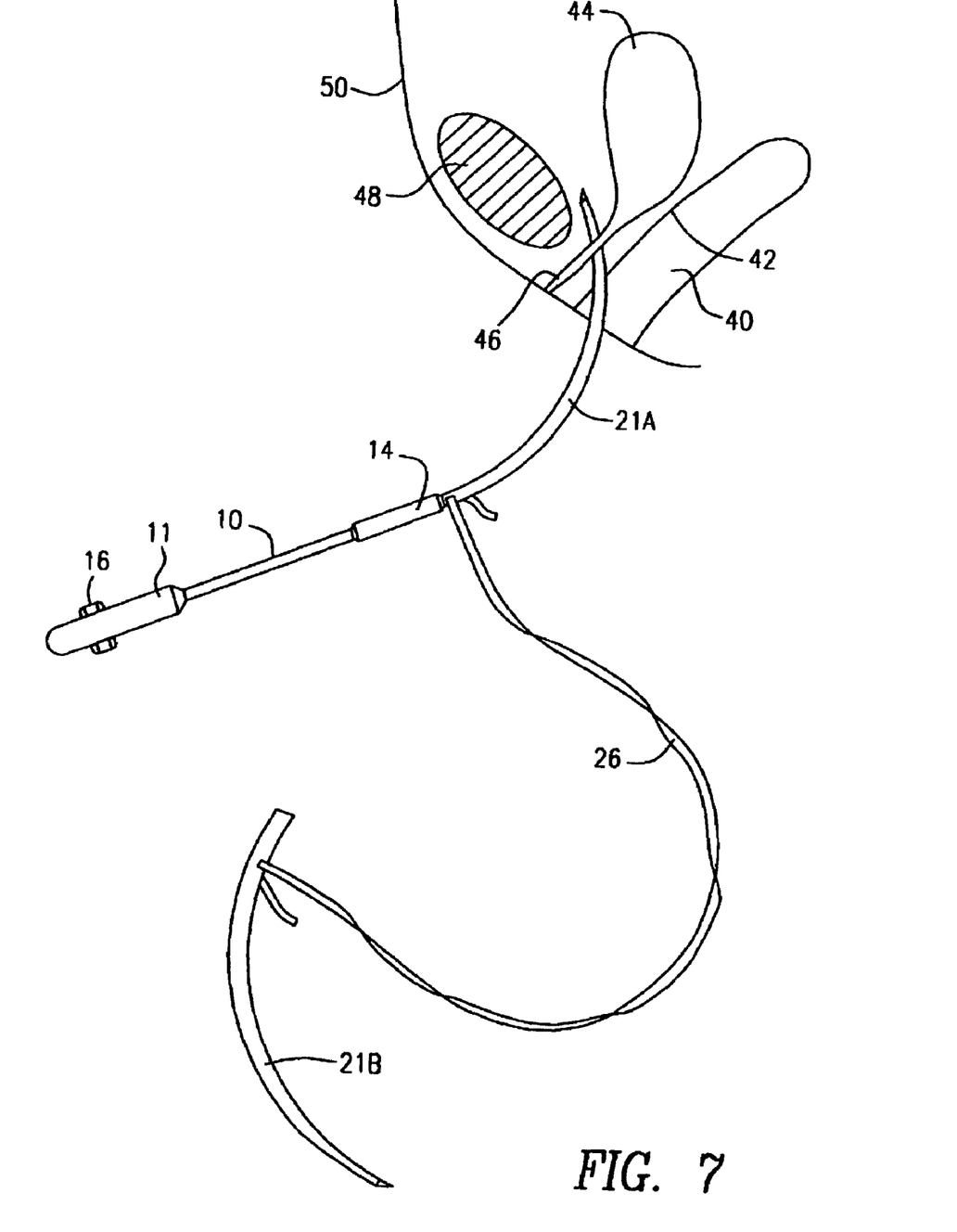
FIGS. 7 to 13 illustrate diagrammatically several surgical steps of the method according to the invention, and FIG. 14 in the same way illustrates the final step of the method.
Figure 8:
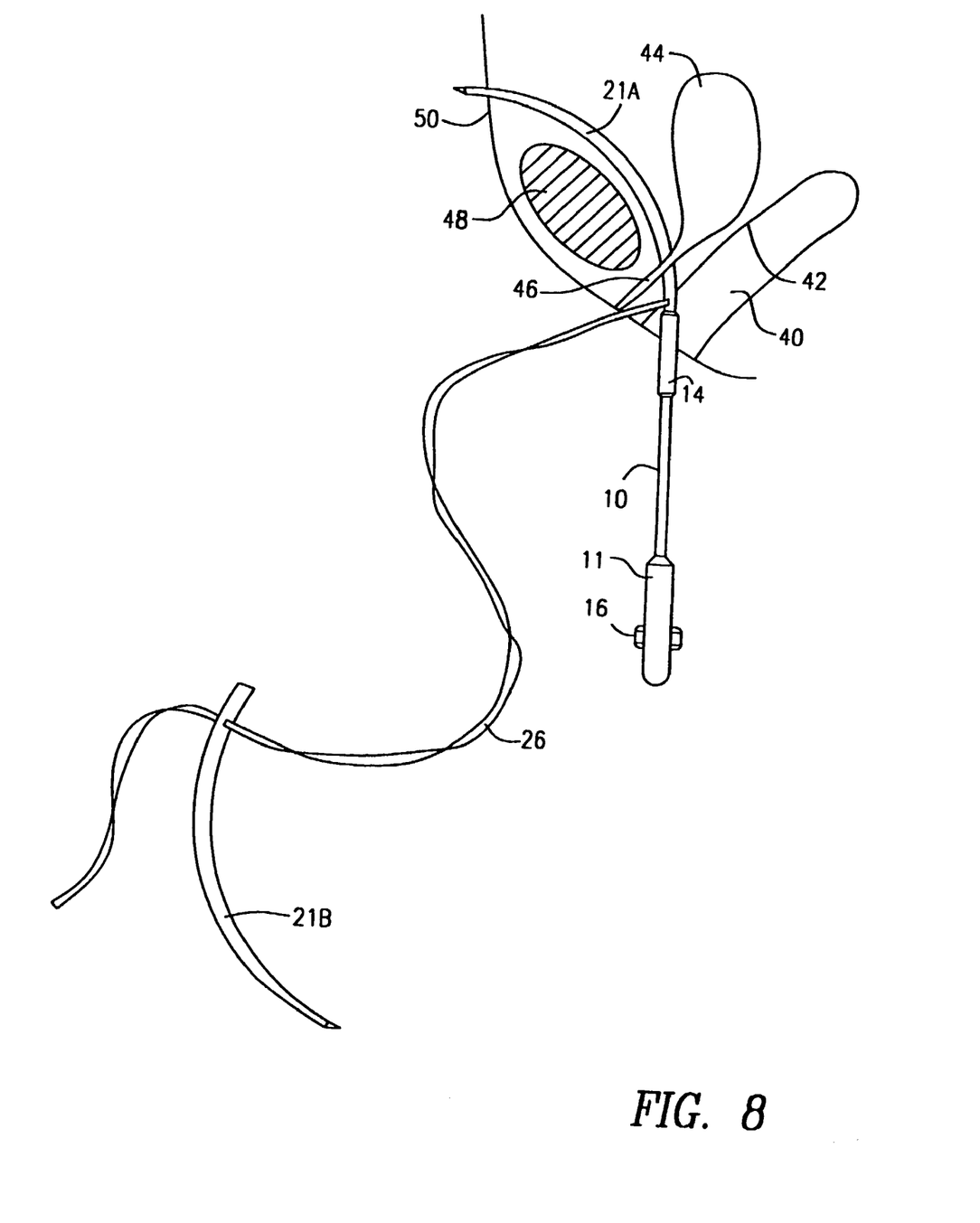

The first step of the surgery for implanting tape 26 is disclosed in FIG. 7 and comprises penetration of the vaginal wall 42 by needle 21A a cut having first been made in said wall 42, and, also penetration of the soft tissue at one side of urethra 46, the needle 21A then, according to FIG. 8, being passed close to the back of the pubic bone 48 and then through the abdominal wall 50 above the pubic bone 48. A cut can be done through the abdominal wall 50 for the passage of the needle 21A therethrough, but if the needle 21A is pointed, it may be sufficient to let the needle 21A penetrate into the abdominal wall 50, from the inside thereof, and to make a registering cut in the abdominal wall 50 on the outside thereof.

Figure 9:
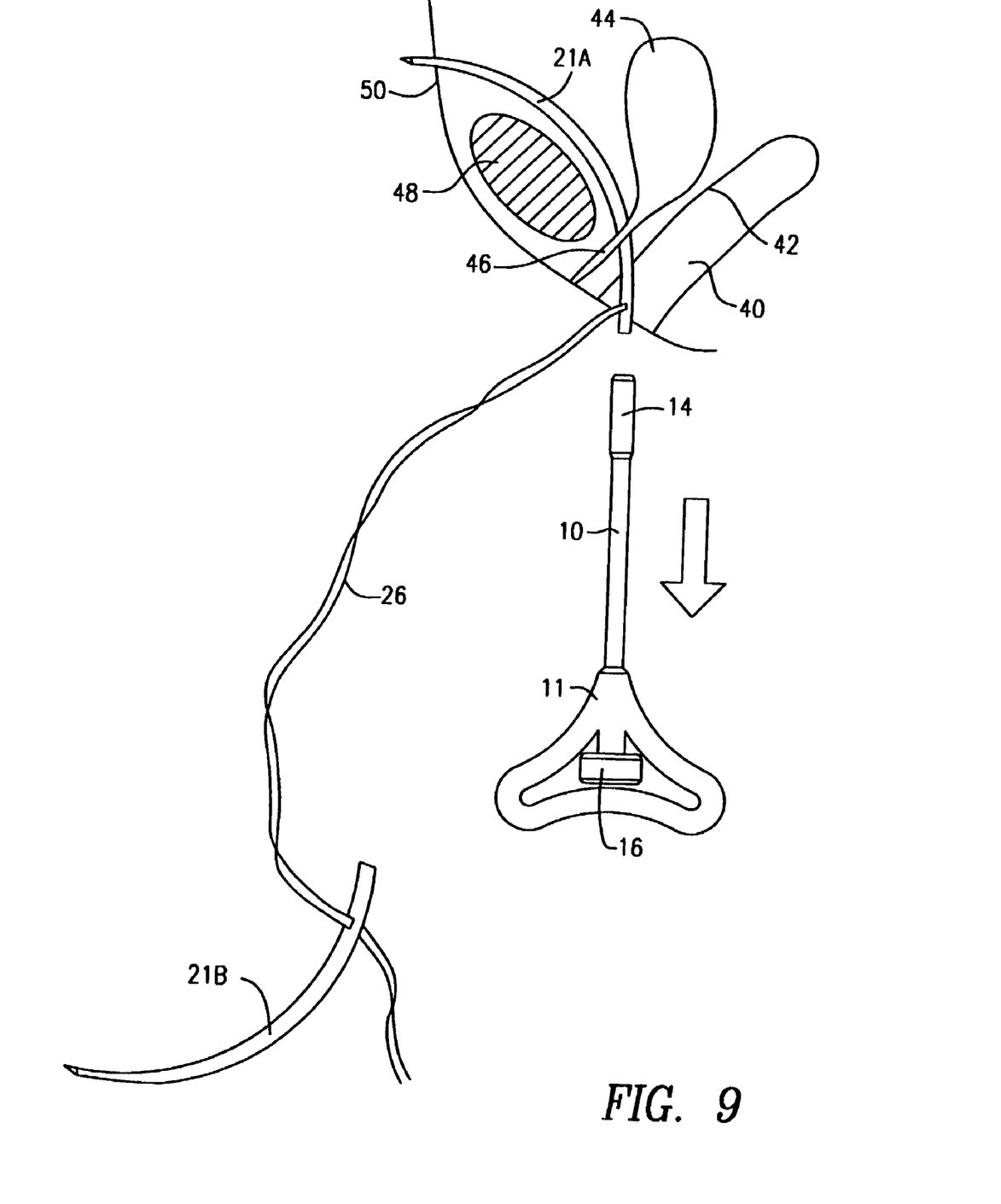
Figure 10:
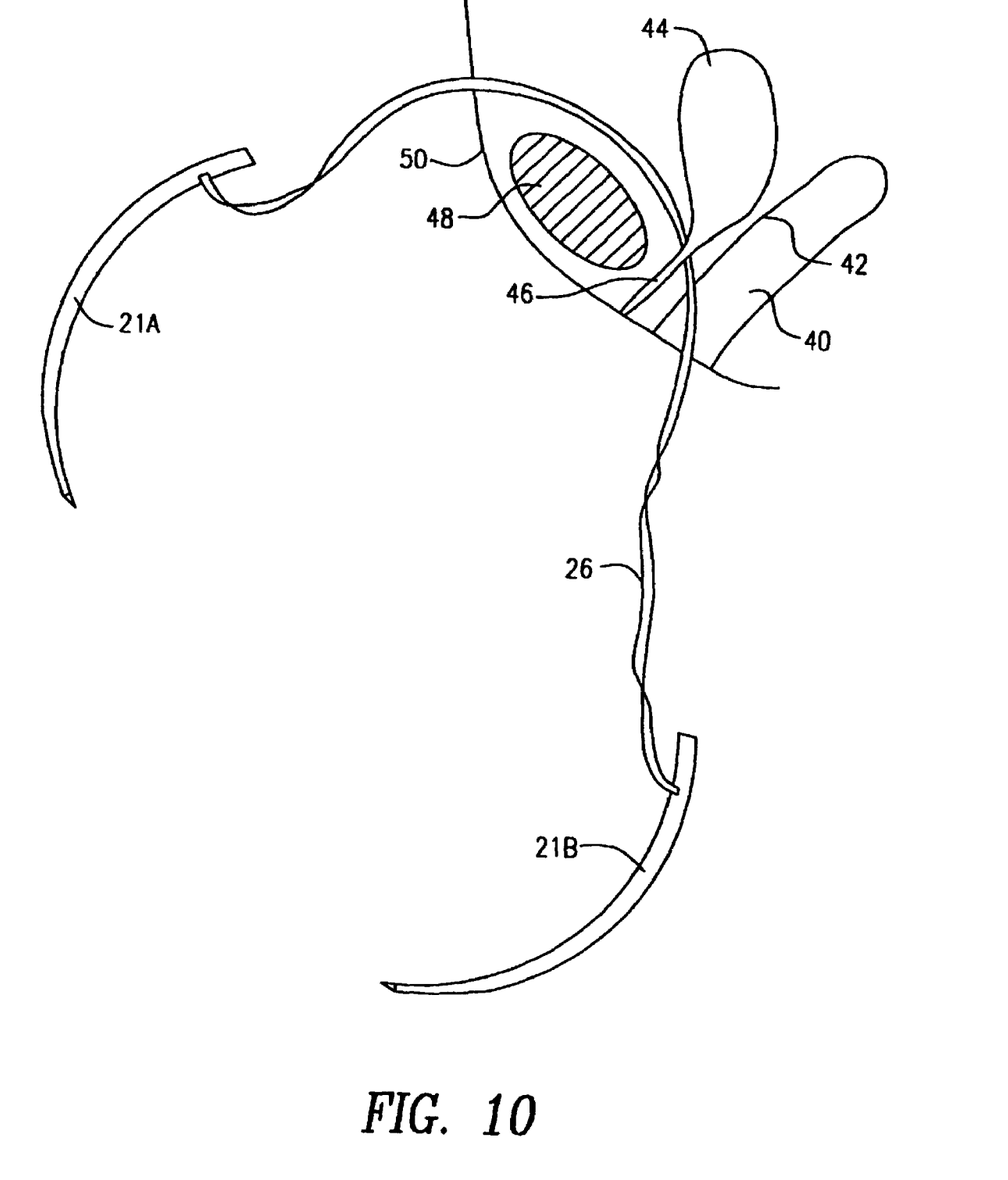

The shank 10 of the instrument is now disconnected from needle 21A, FIG. 9, by rotating shaft 15 at knob 16 so that the threaded portion 18 of the shaft 15 is unscrewed from the threaded portion 23 in needle 21A, the needle 21A then being withdrawn from the abdominal wall 50 by means of forceps and the tape 26 being pulled into and through the tissue as illustrated in FIG. 10.

Figure 11:
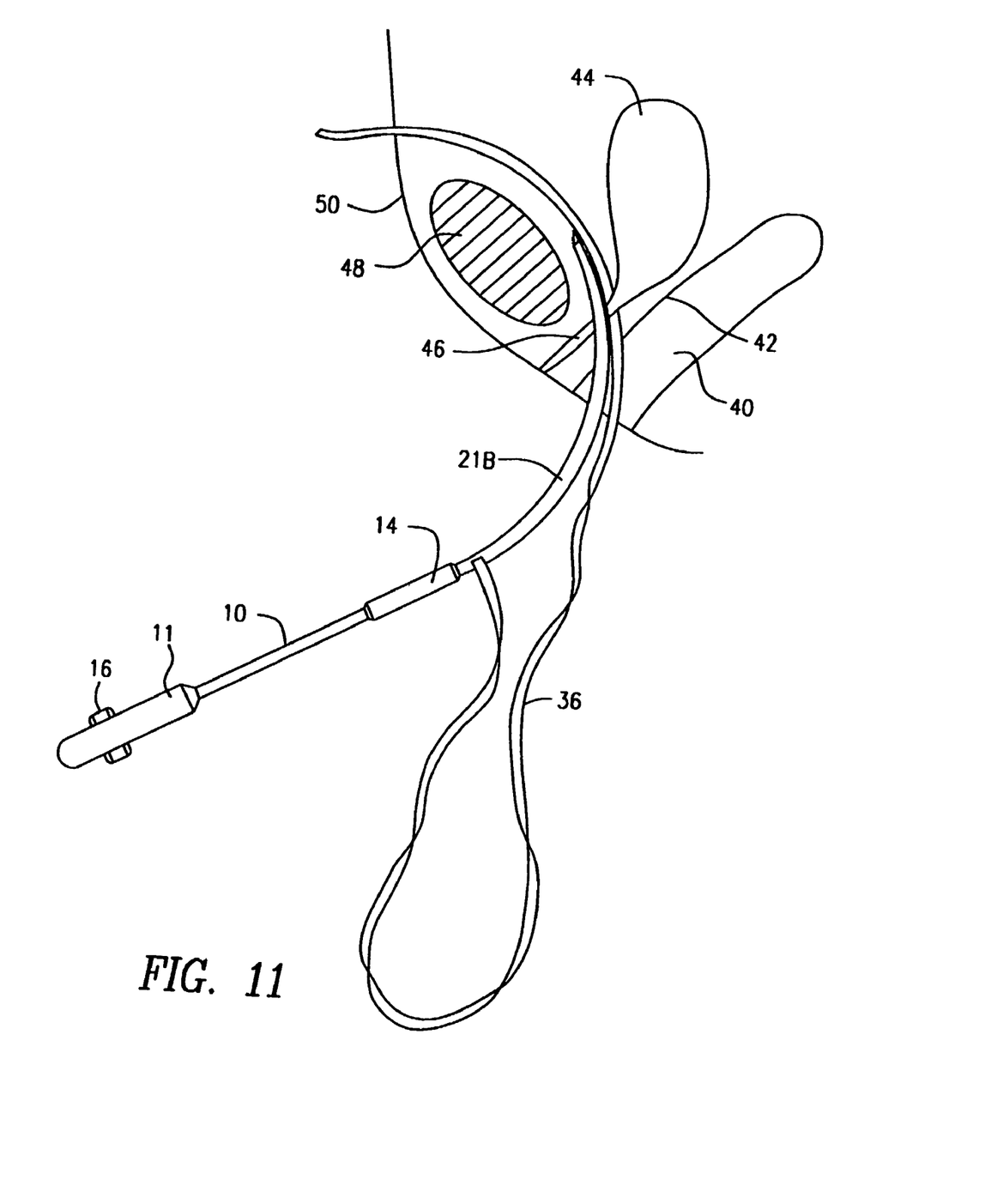
Figure 12:
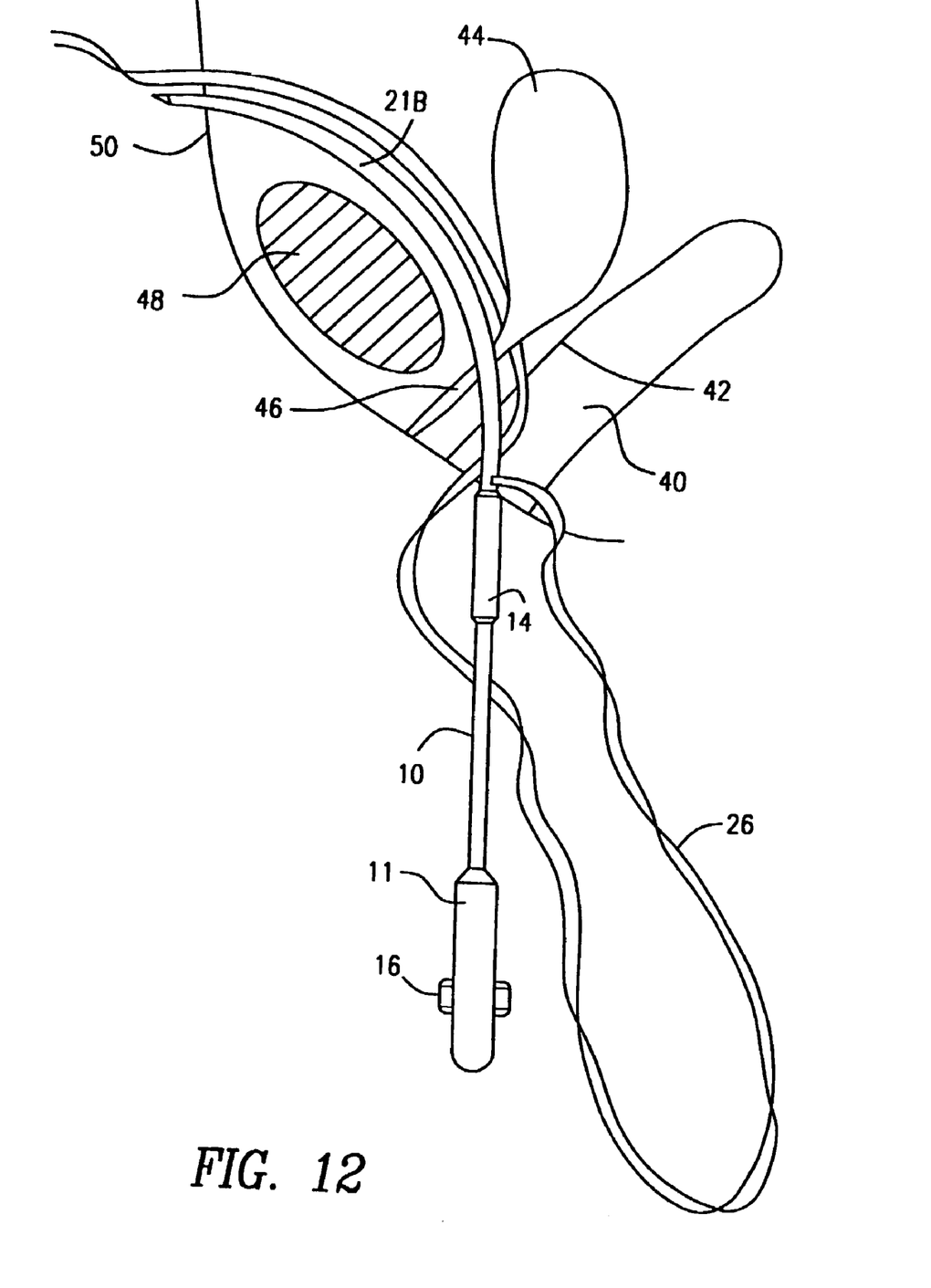

The other needle 21B is now attached to the shank 10, FIG. 11, and is passed through a cut in the vaginal wall 42 to pass through the soft tissue at the other side of the urethra 46. The needle 21B is passed through the abdominal wall 50 (see FIG. 12) and then, after having been disconnected from the shank 10, is withdrawn from the abdominal wall 50 (see FIG. 13), all in the same way as in the earlier procedure with the first needle 21A.

Figure 13:
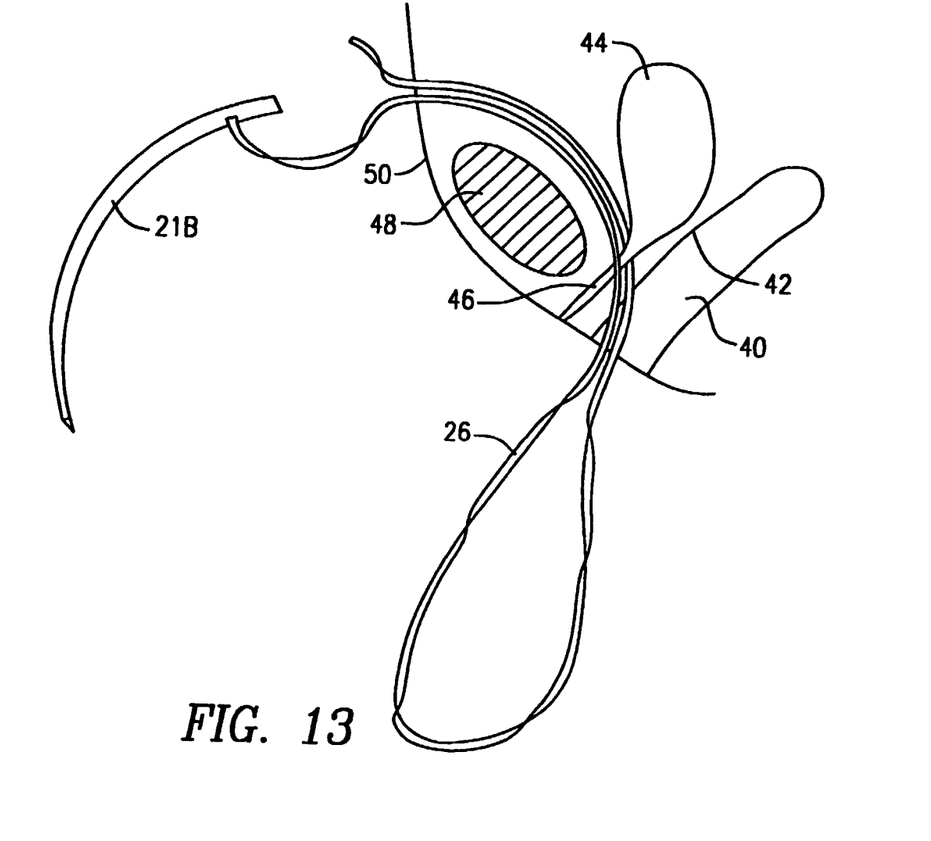
Figure 14:
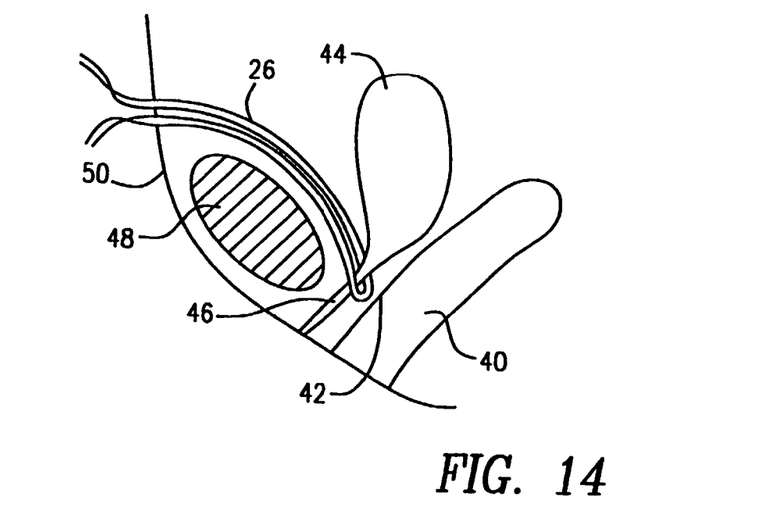

Tape 26 is now located at each side of urethra 46 as shown in FIG. 13 and is tightened with the loop formed by the tape 26 located on the inside surface of the vaginal wall 42 (see FIG. 14). The surplus of the tape 26 at the outside of the abdominal wall 50 is cut off. Then, the tape 26 is left as an implant in the body to form an artificial ligament attached to the abdominal wall 50 and providing the support for the urethra 46 as required in order to restore urinary continence.

Another kind of tape 26, which may be used in the method according to the present invention, can be more closely woven than the tape 26 mentioned above and can be of such material that the tape 26, after a shorter or longer period, will be completely resorbed. By the development of fibroblast proliferation stimulated by the tape 26 the reinforcement of the tissue required in order to restore the urinary continence will be obtained.

I claim:

1. A method for treating female urinary incontinence, comprising the steps of:
   providing a tape that is at least partially enclosed within a sheath that is removably applied to the tape, the sheath including two opposite ends, a longitudinal axis, and a perforation intermediate the opposite ends and generally transverse to the longitudinal axis;
   passing first and second ends of the tape into a female patient's body via the patient's vagina;
   positioning the tape between the patient's vaginal wall and the patient's urethra;
   extending the first and second ends of the tape over the patient's pubic bone and through her abdominal wall such that at least a portion of the tape forms a supportive loop beneath the urethra and such that the first and second ends of the tape extend outside of the patient's body;
   adjusting the position and tension of the supportive loop to achieve a clinically acceptable degree of urinary continence;
   separating the sheath, at the perforation, into two separate sheath portions, each of which is independently removable from the tape; and
   removing each sheath portion from the tape after the first and second ends of the tape are passed through the patient's abdominal wall and extend outside of the patient's body.

2. The method of claim 1, further comprising the steps of:
   attaching a first needle to the first end of the tape before passing the first end into the patient's body; and attaching a second needle to the second end of the tape before passing the second end into the patient's body.

3. The method of claim 1, wherein said passing step further comprises the steps of:
   passing the first end of the tape past one side of the patient's urethra, over the patient's pubic bone and through her abdominal wall; and
   passing the second end of the tape past an opposite side of the patient's urethra, over the patient's pubic bone and through her abdominal wall.

4. The method of claim 1, wherein the tape is substantially flat and flexible.

5. The method of claim 1, wherein the tape comprises netting.

6. The method of claim 1, wherein the sheath includes first and second ends, and wherein said removing step includes the steps of removing the first end of the sheath from the first end of the tape and removing the second end of the sheath from the second end of the tape.

7. The method of claim 1, wherein the sheath and the tape are connected to one another by stitching.

8. A method for treating female urinary incontinence, comprising the steps of:
   at least partially enclosing a tape within a sheath that is removably applied to the tape, the sheath including two opposite ends, a longitudinal axis, and a perforation intermediate the opposite ends and generally transverse to the longitudinal axis;
   passing first and second ends of the tape into a female patient's body;
   positioning at least a portion of the tape between the vaginal wall and the urethra;
   extending the first and second ends of the tape over the patient's pubic bone and through her abdominal wall such that at least a portion of the tape forms a supportive loop beneath the urethra and such that the first and second ends of the tape extend outside of the patient's body;
   adjusting the position and tension of the supportive loop to achieve a clinically acceptable degree of urinary continence;
   pulling on the opposite ends of the sheath, whereby the sheath is split, at the perforation, into two separate sheath portions each of which is independently removable from the tape; and
   removing each sheath portion from the tape after the first and second ends of the tape are passed through the patient's abdominal wall and extend outside of the patient's body.

9. The method of claim 8, wherein the sheath and the tape are connected to one another by stitching.

10. The method of claim 8, wherein said removing step includes the steps of removing one of the sheath portions from the first end of the tape and removing the other of the sheath portions from the second end of the tape.

11. The method of claim 8, further comprising the steps of:
    attaching a first needle to the first end of the tape before passing the first end into the patient's body; and
    attaching a second needle to the second end of the tape before passing the second end into the patient's body.

12. The method of claim 8, wherein said passing step further comprises the steps of:
    passing the first end of the tape past one side of the patient's urethra, over the patient's pubic bone and through her abdominal wall; and
    passing the second end of the tape past an opposite side of the patient's urethra, over the patient's pubic bone and through her abdominal wall.

13. The method of claim 8, wherein the tape is substantially flat and flexible.

14. The method of claim 8, wherein the tape comprises netting.

\* \* \* \* \*